(12) United States Patent
Lacombe et al.

(10) Patent No.: US 6,369,082 B1
(45) Date of Patent: Apr. 9, 2002

(54) CARBOXYLIC ACIDS AND ACYLSULFONAMIDES, COMPOSITIONS CONTAINING SUCH COMPOUNDS AND METHODS OF TREATMENT

(75) Inventors: Patrick Lacombe, Montreal; Marc Labelle, Lazare; Rejean Ruel, St-Lazare, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/662,502

(22) Filed: Sep. 14, 2000

Related U.S. Application Data

(60) Provisional application No. 60/153,903, filed on Sep. 14, 1999.

(51) Int. Cl.[7] .................. C07D 409/04; A61K 31/44
(52) U.S. Cl. .................. 514/333; 514/183; 514/241; 514/242; 514/252.04; 514/255.05; 514/256; 514/336; 514/340; 544/179; 544/180; 544/182; 544/238; 544/333; 544/405; 546/256; 546/268.4; 546/269.1; 546/280.4; 546/281.4
(58) Field of Search ................ 514/333, 336, 514/340; 546/256, 268.4, 280.4

(56) References Cited

U.S. PATENT DOCUMENTS

| | | | |
|---|---|---|---|
| 4,829,081 A | 5/1989 | Damon, II et al. | 514/460 |
| 4,927,851 A | 5/1990 | Damon, II et al. | 514/438 |
| 5,811,459 A | 9/1998 | Breault et al. | 514/555 |

FOREIGN PATENT DOCUMENTS

| | | |
|---|---|---|
| EP | 0 752 421 A1 | 1/1997 |
| WO | WO 87/02662 | 5/1987 |
| WO | WO 96/19469 | 6/1996 |
| WO | WO 97/16442 | 5/1997 |

*Primary Examiner*—Richard L. Raymond
*Assistant Examiner*—Deepak Rao
(74) *Attorney, Agent, or Firm*—Raynard Yuro; Richard C. Billups; David L. Rose

(57) ABSTRACT

This invention encompasses the novel compounds of formula A, which are useful in the treatment of prostaglandin mediated diseases,

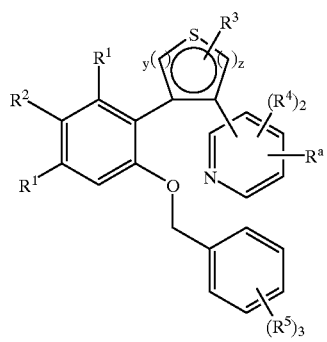

A or a pharmaceutically acceptable salt, hydrate or ester thereof. The invention also encompasses pharmaceutical compositions and methods for treatment of prostaglandin mediated diseases.

23 Claims, No Drawings

CARBOXYLIC ACIDS AND ACYLSULFONAMIDES, COMPOSITIONS CONTAINING SUCH COMPOUNDS AND METHODS OF TREATMENT

CROSS-REFERENCE TO RELATED APPLICATIONS

This application claims the benefit of U.S. Provisional Application Ser. No. 60/153,903, filed on Sep. 14, 1999.

BACKGROUND OF THE INVENTION

This invention relates to compounds and methods for treating prostaglandin mediated diseases, and certain pharmaceutical compositions thereof. More particularly, the compounds of the invention are structurally different from NSAIDs and opiates, and are antagonists of the pain and inflammatory effects of E-type prostaglandins.

Two review articles describe the characterization and therapeutic relevance of the prostanoid receptors as well as the most commonly used selective agonists and antagonists: Eicosanoids: From Biotechnology to Therapeutic Applications, Folco, Samuelsson, Maclouf, and Velo eds, Plenum Press, New York, 1996, chap. 14, 137–154 and Journal of Lipid Mediators and Cell Signalling, 1996, 14, 83–87. An article from The British Journal of Pharmacology (1994, 112, 735–740) suggests that Prostaglandin $E_2$ ($PGE_2$) exerts allodynia through the $EP_1$ receptor subtype and hyperalgesia through $EP_2$ and $EP_3$ receptors in the mouse spinal cord.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects.

In The American Physiological Society (1994, 267, R289-R294), studies suggest that PGE2-induced hyperthermia in the rat is mediated predominantly through the EP1 receptor. World patent applications WO 96/06822 (Mar. 7, 1996), WO 96/11902 (Apr. 25, 1996) and EP 752421-A1 (Jan. 8, 1997) disclose compounds as being useful in the treatment of prostaglandin mediated diseases.

SUMMARY OF THE INVENTION

The present invention relates to compounds of formula A:

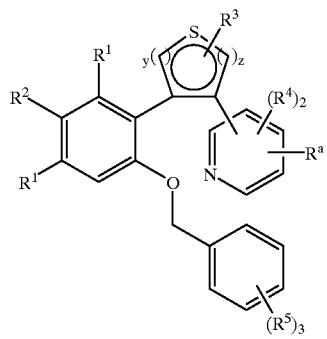

as well as pharmaceutically acceptable salts, hydrates and esters thereof, wherein:

y and z are independently 0–2, such that y+z=2;

$R^a$ is selected from the group consisting of:
1) heteroaryl, wherein heteroaryl is selected from the group consisting of:
   a) furyl,
   b) diazinyl, triazinyl or tetrazinyl,
   c) imidazolyl,
   d) isoxazolyl,
   e) isothiazolyl,
   f) oxadiazolyl,
   g) oxazolyl,
   h) pyrazolyl,
   i) pyrrolyl,
   j) thiadiazloyl,
   k) thiazolyl
   l) thienyl
   m) triazolyl and
   n) tetrazolyl, wherein heteroaryl is optionally substituted with 1–3 substituents independently selected from $R^{11}$ or $C_{1-4}$alkyl,
2) —$COR^6$,
3) —$NR^7R^8$,
4) —$SO_2R^9$,
5) hydroxy,
6) $C_{1-6}$alkoxy, optionally substituted with 1–3 substituents independently selected from $R^{11}$, and
7) $C_{1-6}$alkyl, $C_{2-6}$alkenyl or $C_{3-6}$cycloalkyl, optionally substituted with 1–3 substituents independently selected from $R^{11}$, and further substituted with 1–3 substituents independently selected from the group consisting of:
   (a) —$COR^6$
   (b) —$NR^7R^8$,
   (c) —$SO_2R^9$,
   (d) hydroxy,
   (e) $C_{1-6}$alkoxy or halo$C_{1-6}$alkoxy, and
   (f) heteroaryl,
such that $R^a$ is positioned on the pyridyl ring to which it is bonded in a 1,3 or 1,4 relationship relative to the thienyl group represented in formula A;

$R^1$, $R^2$, $R^3$, $R^4$ and $R^5$ are independently selected from the group consisting of:
1) hydrogen,
2) halogen,
3) $C_{1-6}$alkyl,
4) $C_{1-6}$alkoxy, 5) $C_{1-6}$alkylthio,
6) nitro,
7) carboxy and
8) CN, wherein items (3)–(5) above are optionally substituted with 1–3 substituents independently selected from $R^{11}$;

$R^6$ is selected from the group consisting of hydrogen, hydroxy, $C_{1-6}$alkyl, $C_{1-6}$alkoxy and $NR^7R^8$, wherein $C_{1-6}$alkyl or $C_{1-6}$alkoxy are optionally substituted with 1–3 substituents independently selected from $R^{11}$;

$R^7$ and $R^8$ are independently selected from the group consisting of:
(1) hydrogen,
(2) hydroxy,
(3) $SO_2R^9$
(4) $C_{1-6}$alkyl,
(5) $C_{1-6}$alkoxy,
(6) phenyl,
(7) naphthyl,
(8) furyl,
(9) thienyl and
(10) pyridyl, wherein items (4)–(5) above are optionally substituted with 1–3 substituents independently selected from $R^{11}$, and items (6)–(10) above are optionally substituted with 1–3 substituents independently selected from $R^{11}$ or $C_{1-4}$alkyl, $R^9$ is selected from the group consisting of
(1) hydroxy,
(2) $N(R^{10})_2$,
(3) $C_{1-6}$alkyl, optionally substituted with 1–3 substituents independently selected from $R^{11}$,
(4) phenyl,
(5) naphthyl,
(6) furyl,
(7) thienyl and
(8) pyridyl, wherein items (4)–(8) above are optionally substituted with 1–3 substituents independently selected from $R^{11}$ or $C_{1-4}$alkyl;

$R^{10}$ is hydrogen or $C_{1-6}$alkyl; and $R^{11}$ is selected from the group consisting of: halogen, hydroxy, $C_{1-3}$alkoxy, nitro, $N(R^{10})_2$ and pyridyl.

The invention also encompasses pharmaceutical compositions and methods for treatment or prevention of prostaglandin mediated diseases.

DETAILED DESCRIPTION OF THE INVENTION

The invention is described using the following definitions unless otherwise indicated.

The term "halogen" or "halo" includes F, Cl, Br, and I.

The term "alkyl" means linear, branched or cyclic structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

"Alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

"Alkylthio" means alkylthio groups having the indicated number of carbon atoms of a straight, branched or cyclic configuration. $C_{1-6}$alkylthio, for example, includes methylthio, propylthio, isopropylthio, etc.

"Haloalkyl" means an alkyl group as described above wherein one or more hydrogen atoms have been replaced by halogen atoms, with up to complete substitution of all hydrogen atoms with halo groups. $C_{1-6}$haloalkyl, for example, includes $-CF_3$, $-CF_2CF_3$ and the like.

"Haloalkoxy" means an alkoxy group as described above in which one or more hydrogen atoms have been replaced by halogen atoms, with up to complete substitution of all hydrogen atoms with halo groups. $C_{1-6}$haloalkoxy, for example, includes $-OCF_3$, $-OCF_2CF_3$ and the like.

"Alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

For purposes of this specification, the following abbreviations have the indicated meanings:

BOC=t-butyloxycarbonyl
CBZ=carbobenzoxy
DCC=1,3-dicyclohexylcarbodiimide
DIBAL=diisobutyl aluminum hydride
DIEA=N,N-diisoproylethylamine
DMAP=4-(dimethylamino)pyridine
EDCI=1-(3-dimethylaminopropyl)-3-ethylcarbodiimide hydrochloride
EDTA=ethylenediaminetetraacetic acid, tetrasodium salt hydrate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOBt=1-hydroxybenzotriazole
HRMS=high resolution mass spectrometry
ICBF=isobutyl chloroformate
KHMDS=potassium hexamethyldisilazane
LDA=lithium diisopropylamide
MCPBA=metachloroperbenzoic acid
Ms=methanesulfonyl=mesyl
MsO=methanefulfonate=mesylate
NBS=N-bromosuccinimide
NMM=4-methylmorpholine
PCC=pyridinium chlorochromate
PDC=pyridinium dichromate
Ph=phenyl
PPTS=pyridinium p-toluene sulfonate
pTSA=p-toluene sulfonic acid
r.t.=room temperature
rac.=racemic
TfO =trifluoromethanesulfonate=triflate
TLC=thin layer chromatography Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl In one aspect of the invention, the invention relates to compounds of formula A:

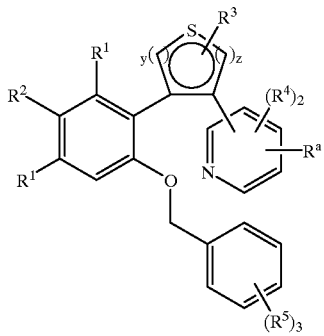

as well as pharmaceutically acceptable salts, hydrates and esters thereof, wherein:
y and z are independently 0–2, such that y+z=2;
$R^a$ is selected from the group consisting of:
1) heteroaryl, wherein heteroaryl is selected from the group consisting of:
   a) furyl,
   b) diazinyl, triazinyl or tetrazinyl,
   c) imidazolyl,
   d) isoxazolyl,
   e) isothiazolyl,
   f) oxadiazolyl,
   g) oxazolyl,
   h) pyrazolyl,
   i) pyrrolyl,
   j) thiadiazloyl,
   k) thiazolyl
   l) thienyl
   m) triazolyl and
   n) tetrazolyl, wherein heteroaryl is optionally substituted with 1–3 substituents independently selected from $R^{11}$ or $C_{1-4}$alkyl,
2) —$COR^6$,
3) —$NR^7R^8$,
4) —$SO_2R^9$,
5) hydroxy,
6) $C_{1-6}$alkoxy, optionally substituted with 1–3 substituents independently selected from $R^{11}$, and
7) $C_{1-6}$alkyl, $C_{2-6}$alkenyl or $C_{3-6}$cycloalkyl, optionally substituted with 1–3 substituents independently selected from $R^{11}$, and further substituted with 1–3 substituents independently selected from the group consisting of:
   (a) —$COR^6$
   (b) —$NR^7R^8$,
   (c) —$SO_2R^9$,
   (d) hydroxy,
   (e) $C_{1-6}$alkoxy or halo$C_{1-6}$alkoxy, and
   (f) heteroaryl,
such that $R^a$ is positioned on the pyridyl ring to which it is bonded in a 1,3 or 1,4 relationship relative to the thienyl group represented in formula A;
$R^1$, $R^2$, $R^3$, $R^4$ and $R^5$ are independently selected from the group consisting of:
1) hydrogen,
2) halogen,
3) $C_{1-6}$alkyl,
4) $C_{1-6}$alkoxy,
5) $C_{1-6}$alkylthio,
6) nitro,
7) carboxy and
8) CN, wherein items (3)–(5) above are optionally substituted with 1–3 substituents independently selected from $R^{11}$;
$R^6$ is selected from the group consisting of hydrogen, hydroxy, $C_{1-6}$alkyl, $C_{1-6}$alkoxy and $NR^7R^8$, wherein $C_{1-6}$alkyl or $C_{1-6}$alkoxy are optionally substituted with 1–3 substituents independently selected from $R^{11}$;
$R^7$ and $R^8$ are independently selected from the group consisting of:
(1) hydrogen,
(2) hydroxy,
(3) $SO_2R^9$
(4) $C_{1-6}$alkyl,
(5) $C_{1-6}$alkoxy,
(6) phenyl,
(7) naphthyl,
(8) furyl,
(9) thienyl and
(10) pyridyl, wherein items (4)–(5) above are optionally substituted with 1–3 substituents independently selected from $R^{11}$, and items (6)–(10) above are optionally substituted with 1–3 substituents independently selected from $R^{11}$ or $C_{1-4}$alkyl,
$R^9$ is selected from the group consisting of
(1) hydroxy,
(2) $N(R^{10})_2$,
(3) $C_{1-6}$alkyl, optionally substituted with 1–3 substituents independently selected from $R^{11}$,
(4) phenyl,
(5) naphthyl,
(6) furyl,
(7) thienyl and
(8) pyridyl, wherein items (4)–(8) above are optionally substituted with 1–3 substituents independently selected from $R^{11}$ or $C_{1-4}$alkyl;
$R^{10}$ is hydrogen or $C_{1-6}$alkyl; and
$R^{11}$ is selected from the group consisting of: halogen, hydroxy, $C_{1-3}$alkoxy, nitro, $N(R^{10})_2$ and pyridyl.

An embodiment of the present invention that is of particular interest relates to compounds of formula A':

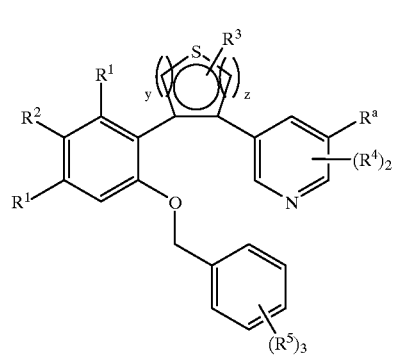

as well as pharmaceutically acceptable salts, hydrates and esters thereof, wherein:
y and z are independently 0–2, such that y+z=2;
$R^a$ is selected from the group consisting of:
1) heteroaryl, wherein heteroaryl is selected from the group consisting of:
   a) furyl,
   b) diazinyl, triazinyl or tetrazinyl, c) imidazolyl,
d) isoxazolyl,
e) isothiazolyl,
f) oxadiazolyl,
g) oxazolyl,
h) pyrazolyl,
i) pyrrolyl,
j) thiadiazloyl,
k) thiazolyl
l) thienyl
m) triazolyl and
n) tetrazolyl, wherein heteroaryl is optionally substituted with 1–3 substituents independently selected from $R^{11}$ or $C_{1-4}$alkyl,
2) —$COR^6$,
3) —$NR^7R^8$,
4) —$SO_2R^9$,
5) hydroxy,
6) $C_{1-6}$alkoxy, optionally substituted with 1–3 substituents independently selected from $R^{11}$, and
7) $C_{1-6}$alkyl, $C_{2-6}$alkenyl or $C_{3-6}$cycloalkyl, optionally substituted with 1–3 substituents independently selected from $R^{11}$, and further substituted with 1–3 substituents independently selected from the group consisting of:
  (a) —$COR^6$
  (b) —$NR^7R^8$,
  (c) —$SO_2R^9$,
  (d) hydroxy,
  (e) $C_{1-6}$alkoxy or halo$C_{1-6}$alkoxy, and
  (f) heteroaryl,
$R^1$, $R^2$, $R^3$, $R^4$ and $R^5$ are independently selected from the group consisting of:
1) hydrogen,
2) halogen,
3) $C_{1-6}$alkyl,
4) $C_{1-6}$alkoxy,
5) $C_{1-6}$alkylthio,
6) nitro,
7) carboxy and
8) CN, wherein items (3)–(5) above are optionally substituted with 1–3 substituents independently selected from $R^{11}$;
$R^6$ is selected from the group consisting of hydrogen, hydroxy, $C_{1-6}$alkyl, $C_{1-6}$alkoxy and $NR^7R^8$, wherein $C_{1-6}$alkyl or $C_{1-6}$alkoxy are optionally substituted with 1–3 substituents independently selected from $R_{11}$;
$R^7$ and $R^8$ are independently selected from the group consisting of:
(1) hydrogen,
(2) hydroxy,
(3) $SO_2R^9$
(4) $C_{1-6}$alkyl,
(5) $C_{1-6}$alkoxy,
(6) phenyl,
(7) naphthyl,
(8) furyl,
(9) thienyl and
(10) pyridyl, wherein items (4)–(5) above are optionally substituted with 1–3 substituents independently selected from $R^{11}$, and items (6)–(10) above are optionally substituted with 1–3 substituents independently selected from $R^{11}$ or $C_{1-4}$alkyl,
$R^9$ is selected from the group consisting of
(1) hydroxy,
(2) $N(R^{10})_2$,
(3) $C_{1-6}$alkyl, optionally substituted with 1–3 substituents independently selected from $R^{11}$,
(4) phenyl,
(5) naphthyl,
(6) furyl,
(7) thienyl and
(8) pyridyl, wherein items (4)–(8) above are optionally substituted with 1–3 substituents independently selected from $R^{11}$ or $C_{1-4}$alkyl;
$R^{10}$ is hydrogen or $C_{1-6}$alkyl; and
$R^{11}$ is selected from the group consisting of: halogen, hydroxy, $C_{1-3}$alkoxy, nitro, $N(R^{10})_2$ and pyridyl.

Another embodiment of the invention that is of particular interest relates to compounds of formula A or A' wherein $R^a$ is selected from the group consisting of: heteroaryl, as originally defined, $COR^6$, wherein $R^6$ is as originally defined, $C_{1-6}$ alkyl and $C_{2-6}$ alkenyl, optionally substituted as originally defined, and $SO_2R^9$ with $R^9$ as originally defined. Within this subset, all other variables are as originally defined.

More particularly, an embodiment of the invention that is of interest relates to a compound of formula A or A' wherein $R^a$ is selected from the group consisting of:

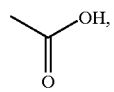
(1)

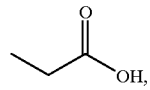
(2)

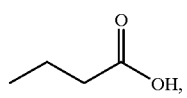
(3)

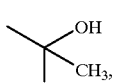
(4)

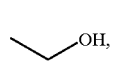
(5)

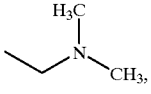
(6)

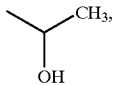
(7)

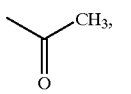
(8)

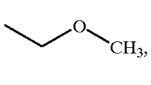
(9)

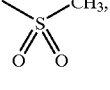
(10)

-continued

(11) 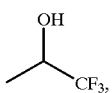

(12) 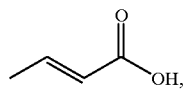

(13) 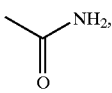

(14) 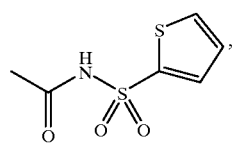

(15) 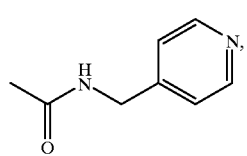

(16) 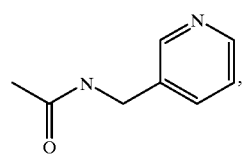

(17) 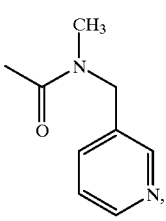

(18) 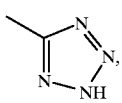

(19) 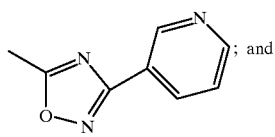; and

(20) 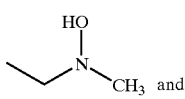 and

(21) 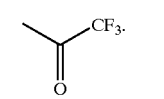

Within this embodiment of the invention, all other variables are as originally defined.

More particularly, a subset of the invention that is of interest relates to compounds of formula A or A' wherein $R^a$ is selected from the group consisting of: $CO_2H$, $CH_2OH$, $C(OH)(CH_3)_2$, $CH(OH)CF_3$ and $C(O)CF_3$. Within this subset, all other variables are as originally defined.

Another embodiment of the invention that is of particular interest relates to compounds of formula A or A' wherein 1–3 of $R^1$ and $R^2$ are selected from the group consisting of halo, $C_{1-4}$ alkyl, $C_{1-4}$ alkoxy, $C_{1-4}$ alkylthio and $NO_2$. Within this subset, all other variables are as originally defined.

Another embodiment of the invention that is of particular interest relates to compounds of formula A or A' wherein each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined. Within this subset, all other variables are as originally defined.

Another embodiment of the invention that is of particular interest relates to compounds of formula A or A' wherein each $R^3$ independently represents a member selected from the group consisting of: H and halo. Within this subset, all other variables are as originally defined.

Another embodiment of the invention that is of particular interest relates to compounds of formula A or A' wherein one of y and z represents 0 and the other represents 2. Within this subset, all other variables are as originally defined.

An embodiment of the invention that is of more particular interest relates to compounds of formula A or A' wherein $R^a$ is selected from the group consisting of: heteroaryl, as originally defined, $COR^6$, wherein $R^6$ is as originally defined, $C_{1-6}$ alkyl and $C_{2-6}$ alkenyl, optionally substituted as originally defined, and $SO_2R^9$ with $R^9$ as originally defined;

$R^1$ and $R^2$ are selected from the group consisting of halo, $C_{1-4}$ alkyl, $C_{1-4}$ alkoxy, $C_{1-4}$ alkylthio and $NO_2$;

$R^4$ and $R^5$ independently represent members selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2. Within this subset, all other variables are as originally defined.

Another embodiment of the invention that is of more particular interest relates to compounds of formula A or A' wherein:

$R^a$ is selected from the group consisting of:

(1) 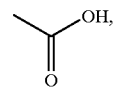

(2) 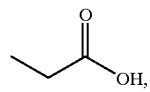

(3) 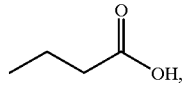

-continued (4) 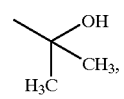

(5) 

(6) 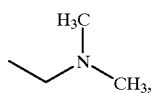

(7) 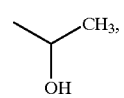

(8) 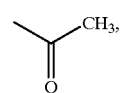

(9) 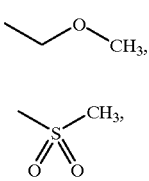

(10) 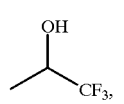

(11) 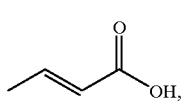

(12) 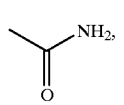

(13) 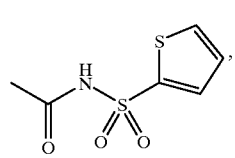

(14) 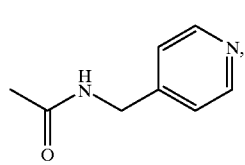

(15) 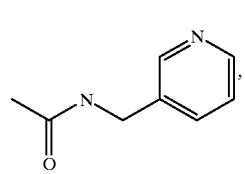

-continued (16)

(17) 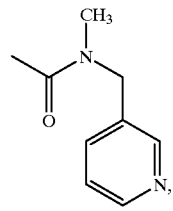

(18) 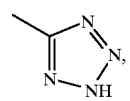

(19) 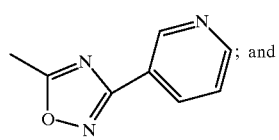

; and

(20) 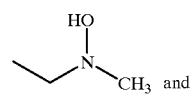

and

(21) 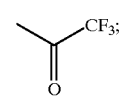

$R^1$ and $R^2$ are selected from the group consisting of halo, $C_{1-4}$ alkyl, $C_{1-4}$ alkoxy, $C_{1-4}$ alkylthio and $NO_2$;

$R^4$ and $R^5$ independently represent members selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2. Within this subset, all other variables are as originally defined.

Another embodiment of the invention that is of more particular interest relates to compounds of formula A or A' wherein:

$R^a$ is selected from the group consisting of: $CO_2H$, $CH_2OH$, $C(OH)(CH_3)_2$, $CH(OH)CF_3$ and $C(O)CF_3$;

$R^1$ and $R^2$ are selected from the group consisting of halo, $C_{1-4}$ alkyl, $C_{1-4}$ alkoxy, $C_{1-4}$ alkylthio and $NO_2$;

$R^4$ and $R^5$ independently represent members selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2. Within this subset, all other variables are as originally defined.

Exemplifying the invention are the following compounds:

(a) 5-{3-[5-chloro-2-(phenylmethoxy)phenyl]-2-thienyl}pyridine-3-carboxylic acid;

(b) (5-{3-[5-chloro-2-(phenylmethoxy)phenyl]-2-thienyl}-3-pyridyl)methan-1-ol;

(c) 2-(5-{3-[5-chloro-2-(phenylmethoxy)phenyl]-2-thienyl}-3-pyridyl)propan-2-ol;

(d) 1-(5-{3-[5-chloro-2-(phenylmethoxy)phenyl](2-thienyl)}(3-pyridyl))-2,2,2-trifluoroethan-1-ol; and
(e) 1-(5-{3-[5-chloro-2-(phenylmethoxy)phenyl](2-thienyl)}(3-pyridyl))-2,2,2-trifluoroethan-1-one.

Another embodiment of the invention is a pharmaceutical composition comprising a compound of formula A or A' in combination with a pharmaceutically acceptable carrier.

Another embodiment of the invention is a method of treating or preventing a prostaglandin mediated disease comprising administering to a mammalian patient in need of such treatment a compound of formula A or A' in an amount which is effective for treating or preventing a prostaglandin mediated disease.

An embodiment of the invention is a method of treating or preventing a prostaglandin mediated disease comprising administering to a mammalian patient in need of such treatment a compound of formula A or A' in an amount which is effective for treating or preventing a prostaglandin mediated disease, wherein the prostaglandin mediated disease is selected from the group consisting of:

(1) pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases;
(2) cellular neoplastic transformations or metastic tumor growth;
(3) diabetic retinopathy and tumor angiogenesis;
(4) prostanoid-induced smooth muscle contraction associated with dysmenorrhea, premature labor, asthma or eosinophil related disorders;
(5) Alzheimer's disease;
(6) glaucoma;
(7) bone loss;
(8) osteoporosis;
(9) promotion of bone formation;
(10) Paget's disease;
(11) cytoprotection in peptic ulcers, gastritis, regional enteritis, ulcerative colitis, diverticulitis or other gastrointestinal lesions;
(12) GI bleeding and patients undergoing chemotherapy;
(13) coagulation disorders selected from hypoprothrombinemia, haemophilia and other bleeding problems;
(14) kidney disease;
(15) thrombosis;
(16) occlusive vascular disease;
(17) presurgery; and
(18) anti-coagulation.

Another embodiment of the invention is a method of treating or preventing a prostaglandin mediated disease comprising administering to a mammalian patient in need of such treatment a compound of formula A in an amount which is effective for treating or preventing a prostaglandin mediated disease, wherein the prostaglandin mediated disease is selected from the group consisting of: pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases.

Another embodiment of the invention is a method of treating or preventing a prostaglandin mediated disease comprising administering to a mammalian patient in need of such treatment a compound of formula A or A' in an amount which is effective for treating or preventing a prostaglandin mediated disease, wherein the prostaglandin mediated disease is pain, fever or inflammation associated with dysmenorrhea.

Another embodiment of the invention is a method of treating or preventing a prostaglandin mediated disease comprising administering to a mammalian patient in need of such treatment a compound of formula A or A' in an amount which is effective for treating, or preventing a prostaglandin mediated disease, wherein the compound is co-administered with other agents or ingredients.

Another embodiment of the invention is a method of treating or preventing a prostaglandin mediated disease comprising administering, to a mammalian patient in need of such treatment a compound of formula A or A' in an amount which is effective for treating or preventing a prostaglandin mediated disease, wherein the compound is co-administered with another agent or ingredient selected from the group consisting of:

(1) an analgesic selected from acetaminophen, phenacetin, aspirin, a narcotic;
(2) a cyclooxygenase-2 selective nonsteroidal anti-inflammatory drug or a conventional nonsteroidal anti-inflammatory drug;
(3) caffeine;
(4) an $H_2$-antagonist;
(5) aluminum or magnesium hydroxide;
(6) simethicone;
(7) a decongestant selected from phenylephrine, phenylpropanolamine, pseudophedrine, oxymetazoline, ephinephrine, naphazoline, xylometazoline, propylhexedrine, or levodesoxyephedrine;
(8) an antitussive selected from codeine, hydrocodone, caramiphen, carbetapentane and dextramethorphan;
(9) another prostaglandin ligand selected from misoprostol, enprostil, rioprostil, ornoprostol and rosaprostol; a diuretic; and
(10) a sedating or non-sedating antihistamine. Examples of COX-2 inhibitors are disclosed in U.S. Pat. Nos. 5,474,995; 5,633,272; and 5,466,823; and in WO 96/125405, WO 97/138986, WO 98/03484, WO 97/114691, and WO 95/10051.

Another embodiment of the invention is a method of treating or preventing a prostaglandin mediated disease comprising administering to a mammalian patient in need of such treatment a compound of formula A or A' in an amount which is effective for treating or preventing a prostaglandin mediated disease, wherein the compound is co-administered with a cyclooxygenase-2selective nonsteroidal anti-inflammatory drug or a conventional nonsteroidal anti-inflammatory drug.

Another embodiment of the invention is a method of treating or preventing a prostaglandin mediated disease comprising administering to a mammalian patient in need of such treatment a compound of formula A or A' in an amount which is effective for treating or preventing a prostaglandin mediated disease, wherein the compound is co-administered with a conventional nonsteroidal anti-inflammatory drug selected from the group consisting of: aspirin, ibuprofen, naproxen, and ketoprofen.

Another embodiment of the invention is a method of treating or preventing a prostaglandin mediated disease comprising administering to a mammalian patient in need of such treatment a compound of formula A or A' in an amount which is effective for treating or preventing a prostaglandin mediated disease, wherein the compound is co-administered with a cyclooxygenase-2 selective nonsteroidal anti-inflammatory drug selected from rofecoxib and celecoxib.

Salts

The pharmaceutical compositions of the present invention comprise a compound of formula or A' as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of formula A or A' are meant to also include the pharmaceutically acceptable salts.

Dose Ranges

The magnitude of prophylactic or therapeutic dose of a compound of formula A or A' will, of course, vary with the nature and the severity of the condition to be treated and with the particular compound of formula A and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 2 g of an active ingredient, typically 25 mg, 50 mg, 100 mg, 200 mg, 300 mg, 400 mg, 500 mg, 600 mg, 800 mg, or 1000 mg.

Pharmaceutical Compositions

For the treatment of any of the prostanoid mediated diseases compounds of formula A may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula A or A' may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula A or A' are employed. (For purposes of this application, topical application shall include mouth washes and gargles.) Topical formulations may generally be comprised of a pharmaceutical carrier, cosolvent, emulsifier, penetration enhancer, preservative system, and emollient.

Utilities

The ability of the compounds of formula A or A' to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: Pain, fever and inflammation of a variety of conditions including rheumatic fever, symptoms associated with influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases. In addition, such a compound may inhibit cellular neoplastic transformations and metastic tumor growth and hence can be used in the treatment of cancer. Compounds of formula A may also be of use in the treatment and/or prevention prostaglandin-mediated proliferation disorders such as may occur in diabetic retinopathy and tumor angiogenesis. Compounds of formula A or A' will also inhibit prostanoid-induced smooth muscle contraction by antagonizing contractile prostanoids or mimicking relaxing prostanoids and hence may be use in the treatment of dysmenorrhea, premature labor, asthma and eosinophil related disorders. It will also be of use in the treatment of Alzheimer's disease, the treatment of glaucoma, for the prevention of bone loss (treatment of osteoporosis) and for the promotion of bone formation (treatment of fractures) and other bone diseases such as Paget's disease.

By virtue of its prostanoid or prostanoid antagonist activity, a compound of formula A or A' will prove useful as an alternative to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; thrombosis, occlusive vascular diseases; those prior to surgery or taking anti-coagulants. Compounds of formula A or A' will also be useful as a cytoprotective agent for patients under chemotherapy.

Combinations with Other Drugs

Compounds of formula A or A' will be useful as a partial or complete substitute for conventional antiinflammatory or analgesic compounds in preparations wherein they are presently co-administered with other agents or ingredients. Thus in further aspects, the invention encompasses pharmaceutical compositions for treating prostaglandin E2 mediated diseases as defined above comprising a non-toxic therapeutically effective amount of the compound of formula A or A' as defined above and one or more ingredients such as another pain reliever including acetaminophen or phenacetin; a COX-2 selective inhibiting agent; a conventional NSAID; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; another prostaglandin ligand including misoprostol, enprostil, rioprostil, ornoprostol or rosaprostol; a diuretic; a sedating or non-sedating antihistamine. In addition, the invention encompasses a method of treating prostaglandin E2 mediated diseases comprising: administration to a patient in need of such treatment a non-toxic therapeutically effective amount of the compound of formula A, optionally co-administered with one or more of such ingredients as listed immediately above.

Methods of Synthesis

Compounds of the present invention can be prepared according to the following methods.

Preparation of Common Intermediates

As illustrated in Scheme 1, the thiophene derivative (3) is prepared by reacting 2-bromophenylbenzyl ether (1) with thiophene 3-boronic acid (2) under conditions such as palladium catalyzed Suzuki's cross coupling reaction. The thiophene derivative (3) can then be brominated selectively at the 2 position using reagents such as NBS in THF/H$_2$O (50:1).

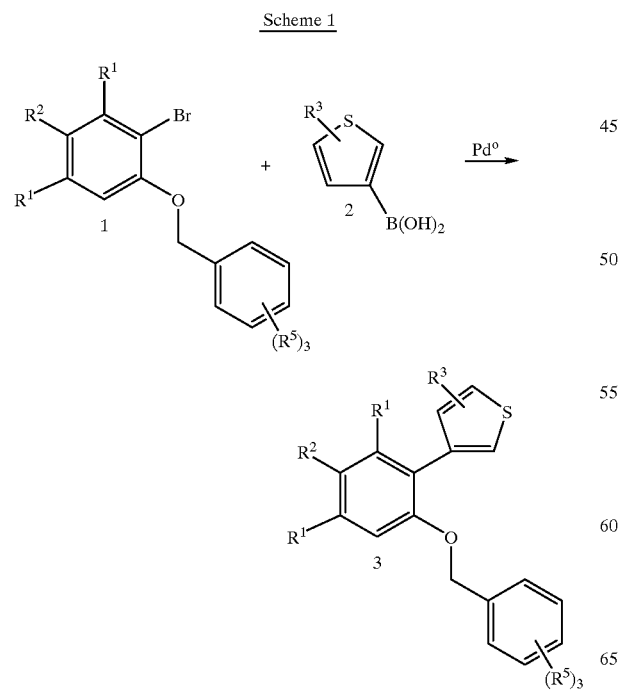

As illustrated in Scheme 2, compound 20 can be prepared via a palladium catalyzed Stille cross coupling reaction of the bromo derivative (19) and stannane (18) which is prepared with hexamethylditin.

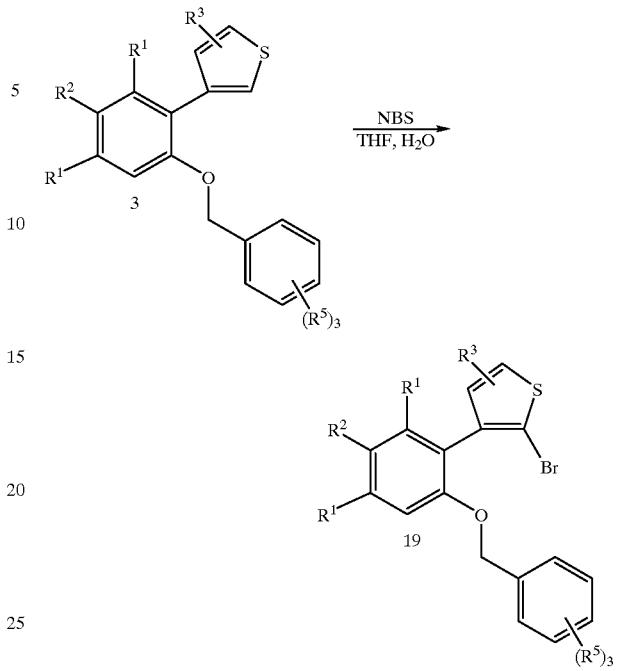

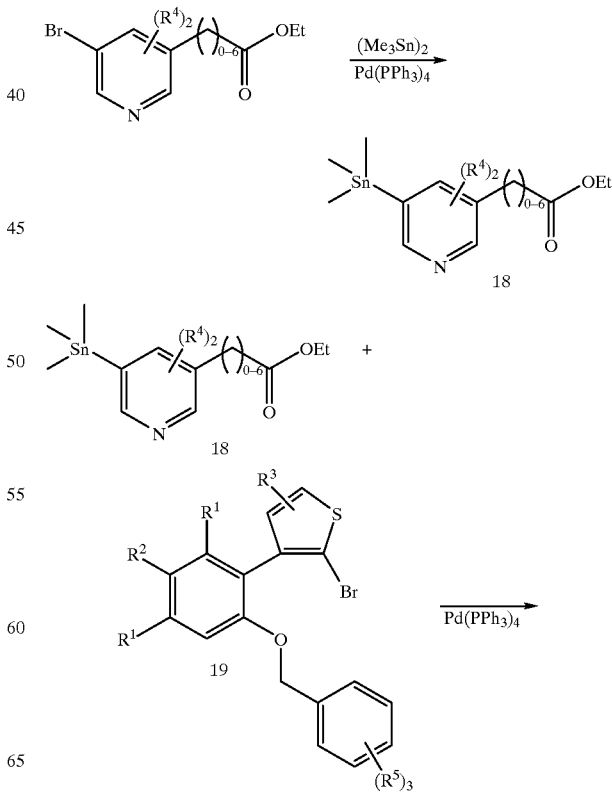

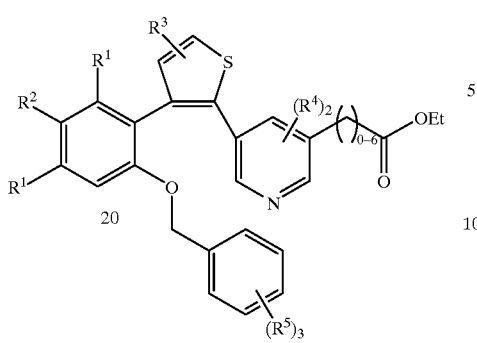
Compound 20 can then be hydrolyzed under basic conditions to give the corresponding acid.
Position isomers of compound 20 can be made according to Schemes 3 and 4 as follows:
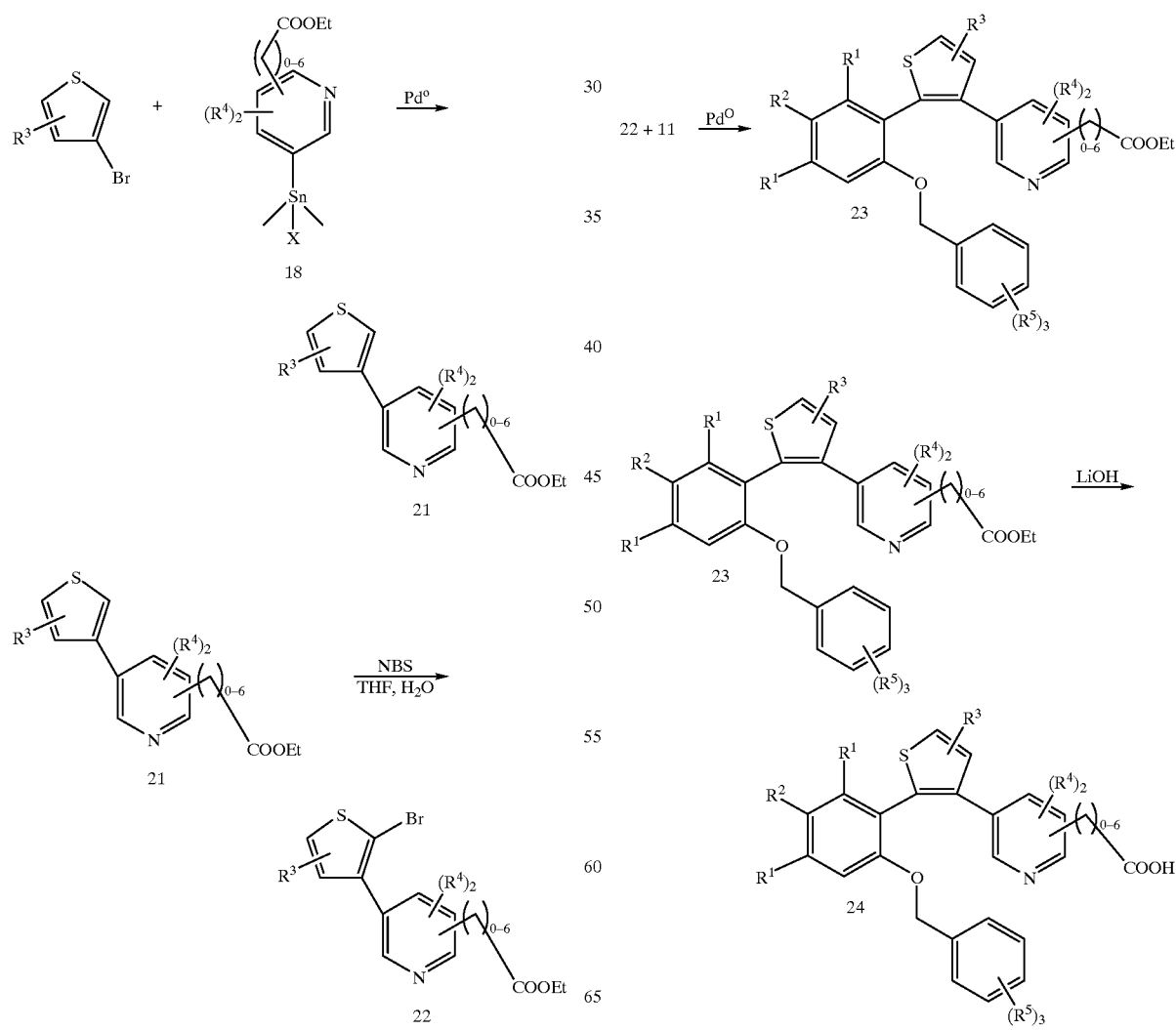

Scheme 4
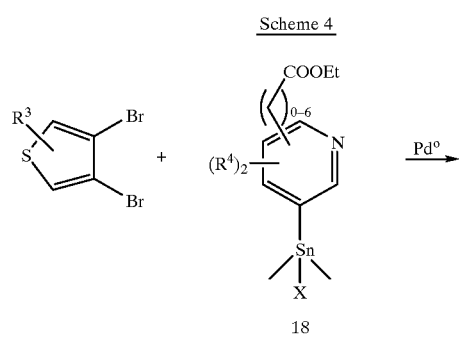
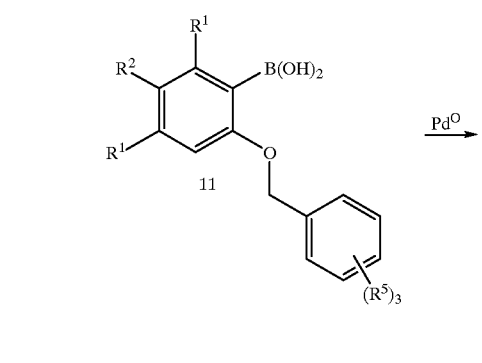
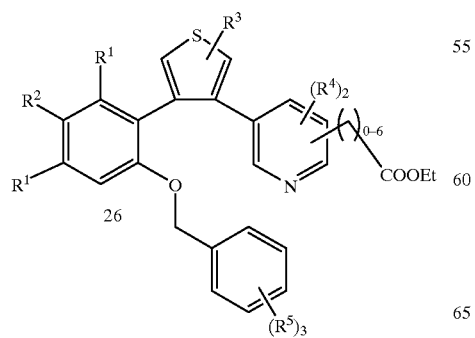
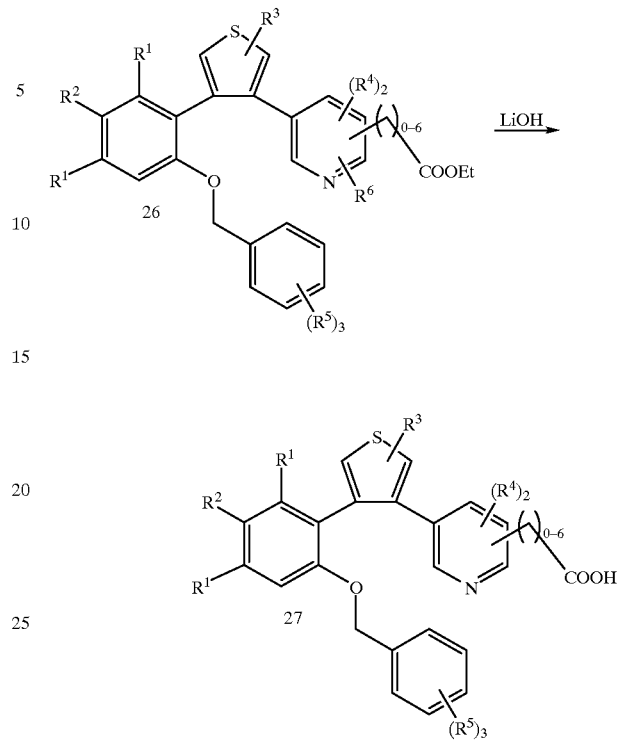
Representative Compounds
Table 1 illustrates compounds of formula A which are representative of the present invention.
TABLE 1
| COMPOUND | EXAMPLE |
|---|---|
|  | 1 |
|  | 2 |

TABLE 1-continued

| COMPOUND | EXAMPLE |
|---|---|
| (structure) | 3 |
| (structure) | 4 |
| (structure) | 5 |
| (structure) | |
| (structure) | |

Assays for Determining Biological Activity

The compound of formula A can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293(ebna) cells. HEK 293(ebna) cells expressing the individual cDNAs are grown under selection and individual colonies are isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 $\mu$M of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 $\mu$M RO-20174 (phosphodiesterase type IV inhibitor, available from Biomol) and, in the case of the $EP_3$ inhibition assay only, 15 $\mu$M forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Rat Paw Edema Assay

The method is the same as described in Chan et al (J. Pharmacol. Exp. Ther. 274:1531–1537, 1995).

LPS-Induced Pyrexia in Conscious Rats

The method is the same as described in Chan et al (J. Pharmacol. Exp. Ther. 274: 1531–1537, 1995).

LPS-Induced Pyrexia in Conscious Squirrel Monkeys

The method is the same as described in Chan et al (Eur. J. Pharmacol. 327: 221–225, 1997).

Acute Inflammatory Hyperalgesia Induced by Carrageenan in Rats

The method is the same as described in Boyce et al (Neuropharmacology 33: 1609–1611, 1994).

Adjuvant-Induced Arthritis in Rats

Female Lewis rats (body weight ~146–170 g) are weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of Mycobacterium butyricum in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day-1) and 21 days following adjuvant injection, and primary paw volumes were determined before (day-1) and on days 4 and 21 following adjuvant injection. The rats were anesthetized with an intramuscular injection of 0.03–0.1 mL of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) were administered per os b.i.d. beginning post injection of adjuvant and continuing for 21 days. The compounds are prepared weekly, refrigerated in the dark until used, and vortex mixed immediately prior to administration.

The invention is further illustrated in connection with the following non-limiting Examples. All the end products of the formula A were analyzed by NMR, TLC and mass spectrometry.

Intermediates were analyzed by NMR and TLC.

Most compounds were purified by flash chromatography on silica gel.

Recrystallization and/or swish (suspension in a solvent followed by filtration of the solid) with a solvent such as ether:hexane 1:1.

The course of reactions was followed by thin layer chromatography (TLC) and reaction times are given for illustration only.

Temperatures are in degrees Celsius.

EXAMPLE 1

5-{3-[5-chloro-2-(phenylmethoxy)phenyl]-2-thienyl}pyridine-3-carboxylic Acid

2-Bromophenylbenzyl ether (3.5 g, 13.3 mmol, prepared from 2-bromophenol following standard benzylation procedure) was reacted with thiophene 3-boronic acid (2.1 g, 16.6 mmol, purchased from Lancaster), tetrakis (triphenylphosphine) palladium (770 mg, 0.7 mmol) and 2M $Na_2CO_3$ (25 mL) in 1,2-dimethoxyethane (75 mL) at 90° C. for 24 hours. The mixture was cooled down and a saturated solution of ammonium chloride and ethyl acetate were added. The separated aqueous layer was extracted with ethyl acetate (3×50 mL) and the combined organic layers were dried ($MgSO_4$ anh.), filtered and evaporated. Flash-chromatography of the residue (ethyl acetate-hexanes 1:10) yielded 3.5 g of thiophene 3 (Scheme 1) which was selectively brominated at the 2 position according to the following procedure:

Thiophene 3 (2.4 g, 9.0 mmol) was treated with N-bromosuccinimide (1.6 g, 9.0 mmol) in THF (50 mL) containing 0.5 mL of water. The mixture was stirred at room temperature for 1.5 hours and water and diethyl ether were added. The separated aqueous layer was extracted with ether (3×50 mL) and the combined organic layers were dried ($MgSO_4$ anh.), filtered and evaporated. Flash-chromatography of the residue (ethyl acetate-hexanes 1:10) yielded 3.1 g of the bromothiophene 19.

To a solution of hexamethylditin (14.22 g, 43.4 mmol) and ethyl 5-bromonicotinate (10.0 g, 43.4 mmol), in toluene (400 ml) is added $Pd(PPh_3)_4$ (2.54 g, 2.2 mmol). The reaction is stirred 3 h at 100° C. then cooled down and evaporated under reduced pressure to give a residu which is purified by flash chromatography (90% Hexanes/10% AcOEt) to afford the desired material 18 (11.06 g, 81%).

To a solution of stannane 18 (10.0 g, 31.85 mmol) and bromo derivative 19 (10.52 g, 27.69 mmol), in DMF (150 ml) is added $Pd_2(dba)_3$ (1.27 g, 1.38 mmol), and $AsPh_3$ (3.39 g, 11.08 mmol). The reaction is stirred at 100° C. overnight, cooled down, diluted with AcOEt, washed with water, brine, $MgSO_4$ and concentrated under reduced pressure to give a residu which is purified by flash chromatography (60% $CH_2Cl_2$/40% Hexanes to 80% $CH_2Cl_2$/20% AcOEt) to provide ethyl ester 20 (8.18 g, 66%) which is hydrolyzed under basic conditions to provide the title compound. $^1H$ nmr (400 MHz, $CD_3COCD_3$) δ ppm 8.99 (1H, s.), 8.52 (1H, s), 8.17 (1H, s), 7.62 (1H, br. s.), 7.32–7.09 (9H, m), 4.92 (2H, s).

EXAMPLE 2

(5-{3-[5-chloro-2-(phenylmethoxy)phenyl]-2-thienyl}-3-pyridyl)methan-1-ol

To a solution of the ethyl ester of example 1 (8.18 g, 18.2 mmol) in a 1:1 mixture of methanol/THF (50 ml/50 ml) is added $NaBH_4$ (6.87 g, 182 mmol) then the mixture refluxed overnight to produce the corresponding aldehyde. The reaction is cooled, quenched with HCl 10%, diluted with AcOEt, washed with $NaHCO_3$, brine, dried (anh. $MgSO_4$) and concentrated under reduced pressure to give a residue which was purified by flash chromatography (70% $CH_2Cl_2$/30% AcOEt) to provide the title compound (2.96 g). $^1H$ nmr (400 MHz, $CD_3COCD_3$) δ ppm 8.45 (1H, d, J=2.0 Hz), 8.32 (1H, d, J=2.3 Hz), 7.68 (1H, d, J=2.2 Hz), 7.53 (1H, d, J=5.2 Hz), 7.29–7.04 (9H, m), 4.89 (3H, s), 4.60 (2H, s).

EXAMPLE 3

2-(5-{3-[5-chloro-2-(phenylmethoxy)phenyl]-2-thienyl}-3-pyridyl)propan-2-ol

To a solution of the ethyl ester of example 1 (34 mg, 0.084 mmol) in ether (1.5 mL) at −78° C. was added MeMgBr (3M in ether, 0.11 mL,0.33 mmol) and the reaction was warmed to room temperature and stirred for 1 h. The mixture was quenched with saturated $NH_4Cl$, diluted with $Et_2O$ and washed successively with HCl 10%, aq. $NaHCO_3$ and brine. The ether layer was dried with anh. $MgSO_4$, filtered and concentrated under reduced pressure to give a residue which was purified by flash chromatography (75% Hexanes/25% AcOEt) to provide the title compound (25.6 mg). $^1$H nmr (400 MHz, CD$_3$COCD$_3$) δ ppm 8.62 (1H, s.), 8.31 (1H, s), 7.66 (1H, s), 7.59 (1H, d, J=7.5 Hz), 7.32–7.11 (9H, m), 4.96 (2H, s), 4.30 (1H, s), 1.39 (6H, s). Elemental analysis calculated for C$_{25}$H$_{23}$Cl$_{12}$NSO$_2$: C, 63.56; H, 4.91; N, 2.96; S, 6.79; found: C, 64.47; H, 5.17; N, 3.06; S, 6.58.

EXAMPLE 4

1-(5-{3-[5-chloro-2-(phenylmethoxy)phenyl](2-thienyl)}(3-pyridyl))-2,2,2-trifluoroethan-1-ol To a solution of the aldehyde of example 2 (1.00 g, 2.46 mmol) in THF (10 ml) at 0° C. was added CF$_3$TMS (0.44 mL, 3.0 mmol) and TBAF (0.25 ml, 1.0M in THF). The reaction was stirred for 2 h. at room temperature and quenched by adding HCl 10%. The mixture was then stirred for 1 h., diluted with AcOEt, washed with HCl 10%, NaHCO$_3$ (aq), brine, dried (anh. MgSO$_4$) and concentrated under reduced pressure to give a residue which was purified by flash chromatography (85% CH$_2$Cl$_2$/15% AcOEt) to provide the title compound (0.90 g). $^1$H nmr (400 MHz, CD$_3$COCD$_3$) δ ppm 8.62 (1H, d, J=1.5 Hz), 8.48 (1H, d, J=2.2 Hz), 7.80 (1H, s), 7.59 (1H, d, J=5.2 Hz), 7.32–7.08 (9H, m), 6.37 (1H, d, J=5.6 Hz), 5.29 (1H, q, J=6.8 Hz), 4.92 (2H, s). Elemental analysis calculated for C$_{24}$H$_{18}$NSF$_3$Cl$_2$O$_2$: C, 56.26; H, 3.54; N, 2.73; S, 6.26: found: C, 56.83; H, 3.64; N, 2.80; S, 6.27.

EXAMPLE 5

1-(5-{3-[5-chloro-2-(phenylmethoxy)phenyl](2-thienyl)}(3-pyridyl))-2,2,2-trifluoroethan-1-one To a solution of the alcohol of example 4 (0.7 g, 1.5 mmol) in dichloromethane was added manganese dioxide (1.26 g, 14.5 mmol) and the slurry was stirred overnight at room temperature. The reaction mixture was then filtered through a pad of celite and the volatils were evaporated under reduced pressure to give a residue which was purified by flash chromatography (70% CH$_2$Cl$_2$/30% AcOEt) to provide the title compound (0.33 g). 1H nmr (400 MHz, acetone-d$_6$) δ ppm 8.78 (1H, d, J=2.1 Hz), 8.48 (1H, d, J =2.2 Hz), 7.96 (1H, t, J=2.1 Hz), 7.60 (1H, d, J=5.1 Hz), 7.35–7.05 (9H, m), 4.94 (2H, s).

What is claimed is:

1. A compound represented by formula A:

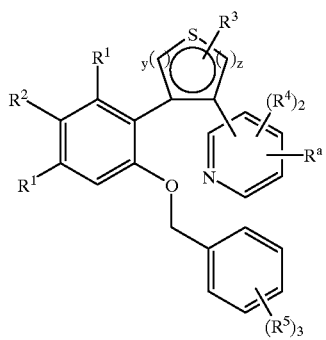

A or a pharmaceutically acceptable salt, hydrate or ester thereof, wherein:

y and z are independently 0–2, such that y+z=2;

R$^a$ is selected from the group consisting of:
1) heteroaryl, wherein heteroaryl is selected from the group consisting of:
   a) furyl,
   b) diazinyl, triazinyl or tetrazinyl,
   c) imidazolyl,
   d) isoxazolyl,
   e) isothiazolyl,
   f) oxadiazolyl,
   g) oxazolyl,
   h) pyrazolyl,
   i) pyrrolyl,
   j) thiadiazloyl,
   k) thiazolyl
   l) thienyl
   m) triazolyl and
   n) tetrazolyl, wherein heteroaryl is optionally substituted with 1–3 substituents independently selected from R$^{11}$ or C$_{1-4}$alkyl,
2) —COR$^6$,
3) —NR$^7$R$^8$,
4) —SO$_2$R$^9$,
5) hydroxy,
6) C$_{1-6}$alkoxy, optionally substituted with 1–3 substituents independently selected from R$^{11}$, and
7) C$_{1-6}$alkyl, C$_{2-6}$alkenyl or C$_{3-6}$cycloalkyl, optionally substituted with 1–3 substituents independently selected from R$^{11}$, and further substituted with 1–3 substituents independently selected from the group consisting of:
   (a) —COR$^6$
   (b) —NR$^7$R$^8$,
   (c) —SO$_2$R$^9$,
   (d) hydroxy,
   (e) C$_{1-6}$alkoxy or haloC$_{1-6}$alkoxy, and
   (f) heteroaryl, such that R$^a$ is positioned on the pyridyl ring to which it is bonded in a 1,3 or 1,4 relationship relative to the thienyl group represented in formula A;

R$^1$, R$^2$, R$^3$, R$^4$ and R$^5$ are independently selected from the group consisting of:
1) hydrogen,
2) halogen,
3) C$_{1-6}$alkyl,
4) C$_{1-6}$alkoxy,
5) C$_{1-6}$alkylthio,
6) nitro,
7) carboxy and
8) CN, wherein items (3)–(5) above are optionally substituted with 1–3 substituents independently selected from R$^{11}$;

R$^6$ is selected from the group consisting of hydrogen, hydroxy, C$_{1-6}$alkyl, C$_{1-6}$alkoxy and NR$^7$R$^8$, wherein C$_{1-6}$alkyl or C$_{1-6}$alkoxy are optionally substituted with 1–3 substituents independently selected from R$^{11}$;

R$^7$ and R$^8$ are independently selected from the group consisting of:
(1) hydrogen,
(2) hydroxy,
(3) SO$_2$R$^9$
(4) C$_{1-6}$alkyl,
(5) C$_{1-6}$alkoxy,
(6) phenyl,
(7) naphthyl,
(8) furyl,
(9) thienyl and
(10) pyridyl, wherein items (4)–(5) above are optionally substituted with 1–3 substituents independently selected from R$^{11}$, and items (6)–(10) above are optionally substituted with 1–3 substituents independently selected from R$^{11}$ or C$_{1-4}$alkyl, R$^9$ is selected from the group consisting of (1) hydroxy,
(2) N(R$^{10}$)$_2$,
(3) C$_{1-6}$alkyl, optionally substituted with 1–3 substituents independently selected from R$^{11}$,
(4) phenyl,
(5) naphthyl,
(6) furyl,
(7) thienyl and
(8) pyridyl, wherein items (4)–(8) above are optionally substituted with 1–3 substituents independently selected from R$^{11}$ or C$_{1-4}$alkyl;

R$^{10}$ is hydrogen or C$_{1-6}$alkyl; and

R$^{11}$ is selected from the group consisting of: halogen, hydroxy, C$_{1-3}$alkoxy, nitro, N(R$^{10}$)$_2$ and pyridyl.

2. A compound in accordance with claim 1 wherein R$^a$ is selected from the group consisting of: heteroaryl, as originally defined, COR$^6$, wherein R$^6$ is as originally defined, C$_{1-6}$ alkyl and C$_{2-6}$ alkenyl, optionally substituted as originally defined, and SO$_2$R$^9$ with R$^9$ as originally defined.

3. A compound in accordance with claim 2 wherein R$^a$ is selected from the group consisting of:

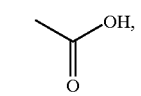 (1)

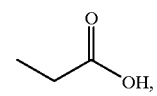 (2)

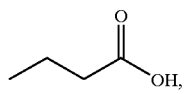 (3)

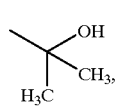 (4)

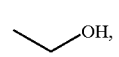 (5)

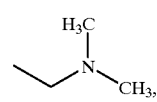 (6)

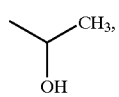 (7)

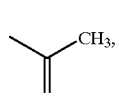 (8)

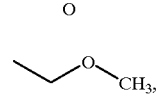 (9)

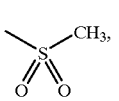 (10)

-continued

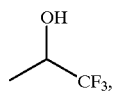 (11)

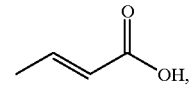 (12)

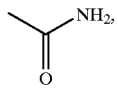 (13)

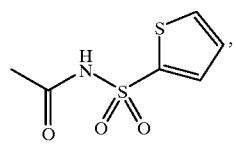 (14)

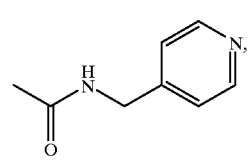 (15)

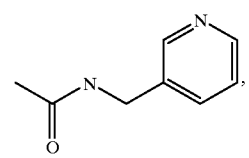 (16)

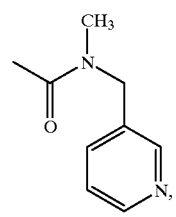 (17)

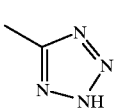 (18)

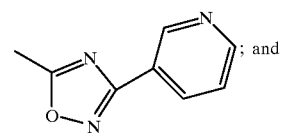 ; and (19)

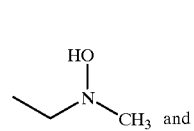 and (20)

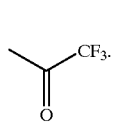 (21)

4. A compound in accordance with claim 2 wherein $R^a$ is selected from the group consisting of: $CO_2H$, $CH_2OH$, $C(OH)(CH_3)_2$, $CH(OH)CF_3$ and $C(O)CF_3$.

5. A compound in accordance with claim 1 wherein 1–3 of $R^1$ and $R^2$ are selected from the group consisting of halo, $C_{1-4}$ alkyl, $C_{1-4}$ alkoxy, $C_{1-4}$ alkylthio and $NO_2$.

6. A compound in accordance with claim 1 wherein $R^4$ and $R^5$ independently represent members selected from the group consisting of: H, halo, $C_{1-6}$ alkyl and $C_{1-6}$ alkoxy, said alkyl and alkoxy groups being optionally substituted as originally defined.

7. A compound in accordance with claim 1 wherein each $R^3$ independently represents a member selected from the group consisting of: H and halo.

8. A compound in accordance with claim 1 wherein one of y and z represents 0 and the other represents 2.

9. A compound in accordance with claim 1 wherein:

$R^a$ is selected from the group consisting of: heteroaryl, as originally defined, $COR^6$, wherein $R^6$ is as originally defined, $C_{1-6}$ alkyl and $C_{2-6}$ alkenyl, optionally substituted as originally defined, and $SO_2R^9$ with $R^9$ as originally defined;

1–3 of $R^1$ and $R^2$ are selected from the group consisting of halo, $C_{1-4}$ alkyl, $C_{1-4}$ alkoxy, $C_{1-4}$ alkylthio and $NO_2$;

each $R^4$ and $R^5$ independently represents a member selected from the group consisting of: H, halo, $C_{1-6}$ alkyl and $C_{1-6}$ alkoxy, said alkyl and alkoxy groups being optionally substituted as originally defined;

each $R^3$ independently represents a member selected from the group consisting of: H and halo;

and one of y and z represents 0 and the other represents 2.

10. A compound in accordance with claim 1 wherein:

$R^a$ is selected from the group consisting of:

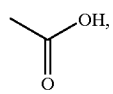
(1)

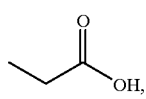
(2)

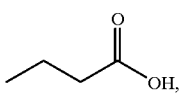
(3)

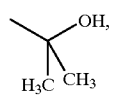
(4)

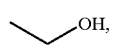
(5)

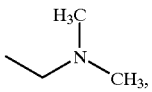
(6)

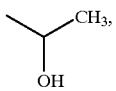
(7)

-continued

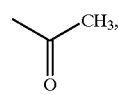
(8)

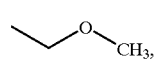
(9)

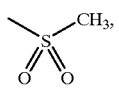
(10)

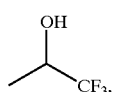
(11)

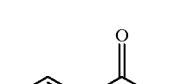
(12)

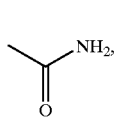
(13)

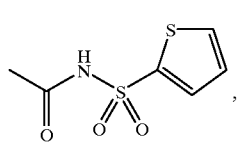
(14)

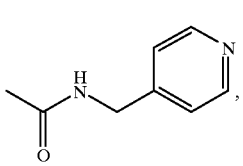
(15)

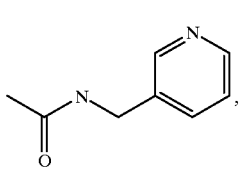
(16)

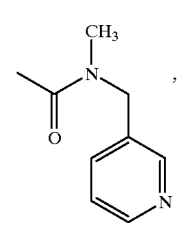
(17)

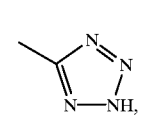
(18)

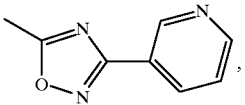
(19)

-continued

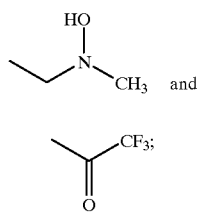

R¹ and R² are selected from the group consisting of halo, $C_{1-4}$ alkyl, $C_{1-4}$ alkoxy, $C_{1-4}$ alkylthio and $NO_2$;

R⁴ and R⁵ independently represent members selected from the group consisting of: H, halo, $C_{1-6}$ alkyl and $C_{1-6}$ alkoxy, said alkyl and alkoxy groups being optionally substituted as originally defined;

each R³ independently represents a member selected from the group consisting of: H and halo;

and one of y and z represents 0 and the other represents 2.

11. A compound in accordance with claim 1 wherein:

$R^a$ is selected from the group consisting of: $CO_2H$, $CH_2OH$, $C(OH)(CH_3)_2$, $CH(OH)CF_3$ and $C(O)CF_3$;

R¹ and R² are selected from the group consisting of halo, $C_{1-4}$ alkyl, $C_{1-4}$ alkoxy, $C_{1-4}$ alkylthio and $NO_2$;

R⁴ and R⁵ independently represent members selected from the group consisting of: H, halo, $C_{1-6}$ alkyl and $C_{1-6}$ alkoxy, said alkyl and alkoxy groups being optionally substituted as originally defined;

each R³ independently represents a member selected from the group consisting of: H and halo;

and one of y and z represents 0 and the other represents 2.

12. A compound selected from the group consisting of:

(a) 5-{3-[5-chloro-2-(phenylmethoxy)phenyl]-2-thienyl}pyridine-3-carboxylic acid;
(b) (5-{3-[5-chloro-2-(phenylmethoxy)phenyl]-2-thienyl}-3-pyridyl)methan-1-ol;
(c) 2-(5-{3-[5-chloro-2-(phenylmethoxy)phenyl]-2-thienyl}-3-pyridyl)propan-2-ol;
(d) 1-(5-{3-[5-chloro-2-(phenylmethoxy)phenyl](2-thienyl)}(3-pyridyl))-2,2,2-trifluoroethan-1-ol; and
(e) 1-(5-{3-[5-chloro-2-(phenylmethoxy)phenyl](2-thienyl)}(3-pyridyl))-2,2,2-trifluoroethan-1-one, or a pharmaceutically acceptable salt thereof.

13. A compound represented by formula A':

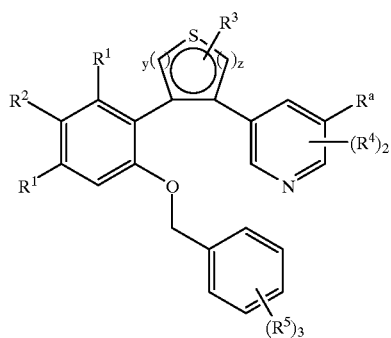

A' or a pharmaceutically acceptable salt, hydrate or ester thereof, wherein:

y and z are independently 0–2, such that y+z=2;

$R^a$ is selected from the group consisting of:
1) heteroaryl, wherein heteroaryl is selected from the group consisting of:
   a) furyl,
   b) diazinyl, triazinyl or tetrazinyl,
   c) imidazolyl,
   d) isoxazolyl,
   e) isothiazolyl,
   f) oxadiazolyl,
   g) oxazolyl,
   h) pyrazolyl,
   i) pyrrolyl,
   j) thiadiazloyl,
   k) thiazolyl
   l) thienyl
   m) triazolyl and
   n) tetrazolyl, wherein heteroaryl is optionally substituted with 1–3 substituents independently selected from $R^{11}$ or $C_{1-4}$alkyl,
2) —COR⁶,
3) —NR⁷R⁸,
4) —SO₂R⁹,
5) hydroxy,
6) $C_{1-6}$alkoxy, optionally substituted with 1–3 substituents independently selected from $R^{11}$, and
7) $C_{1-6}$alkyl, $C_{2-6}$alkenyl or $C_{3-6}$cycloalkyl, optionally substituted with 1–3 substituents independently selected from $R^{11}$, and further substituted with 1–3 substituents independently selected from the group consisting of:
   (a) —COR⁶
   (b) —NR⁷R⁸,
   (c) —SO₂R⁹,
   (d) hydroxy,
   (e) $C_{1-6}$alkoxy or halo$C_{1-6}$alkoxy, and
   (f) heteroaryl;

R¹, R², R³, R⁴ and R⁵ are independently selected from the group consisting of:
1) hydrogen,
2) halogen,
3) $C_{1-6}$alkyl,
4) $C_{1-6}$alkoxy,
5) $C_{1-6}$alkylthio,
6) nitro,
7) carboxy and
8) CN, wherein items (3)–(5) above are optionally substituted with 1–3 substituents independently selected from $R^{11}$;

R⁶ is selected from the group consisting of hydrogen, hydroxy, $C_{1-6}$alkyl, $C_{1-6}$alkoxy and $NR^7R^8$, wherein $C_{1-6}$alkyl or $C_{1-6}$alkoxy are optionally substituted with 1–3 substituents independently selected from $R^{11}$;

R⁷ and R⁸ are independently selected from the group consisting of:
(1) hydrogen,
(2) hydroxy,
(3) SO₂R⁹
(4) $C_{1-6}$alkyl,
(5) $C_{1-6}$alkoxy,
(6) phenyl,
(7) naphthyl,
(8) furyl,
(9) thienyl and
(10) pyridyl, wherein items (4)–(5) above are optionally substituted with 1–3 substituents independently selected from $R^{11}$, and items (6)–(10) above are optionally substituted with 1–3 substituents independently selected from $R^{11}$ or $C_{1-4}$alkyl, $R^9$ is selected from the group consisting of
(1) hydroxy,
(2) $N(R^{10})_2$,
(3) $C_{1-6}$alkyl, optionally substituted with 1–3 substituents independently selected from $R^{11}$,
(4) phenyl,
(5) naphthyl,
(6) furyl,
(7) thienyl and
(8) pyridyl, wherein items (4)–(8) above are optionally substituted with 1–3 substituents independently selected from $R^{11}$ or $C_{1-4}$alkyl;

$R^{10}$ is hydrogen or $C_{1-6}$alkyl; and $R^{11}$ is selected from the group consisting of: halogen, hydroxy, $C_{1-3}$alkoxy, nitro, $N(R^{10})_2$ and pyridyl.

14. A pharmaceutical composition comprising a compound in accordance with claim 1 in combination with a pharmaceutically acceptable carrier.

15. A method of treating a prostaglandin mediated disease comprising administering to a mammalian patient in need of such treatment a compound according to claim 1 in an amount which is effective for treating a prostaglandin mediated disease.

16. A method according to claim 15 wherein the prostaglandin mediated disease is selected from the group consisting of:
(1) pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, rheumatoid arthritis, degenerative joint diseases (osteoarthritis), gout and ankylosing spondylitis, bursitis, burns, radiation and corrosive chemical injuries, sunburns, pain following surgical and dental procedures as well as immune and autoimmune diseases;
(2) cellular neoplastic transformations or metastic tumor growth;
(3) diabetic retinopathy and tumor angiogenesis;
(4) prostanoid-induced smooth muscle contraction associated with dysmenorrhea, premature labor, asthma or eosinophil related disorders;
(5) Alzheimer's disease;
(6) glaucoma;
(7) bone loss;
(8) osteoporosis;
(9) promotion of bone formation;
(10) Paget's disease;
(11) cytoprotection in peptic ulcers, gastritis, regional enteritis, ulcerative colitis, diverticulitis or other gastrointestinal lesions;
(12) GI bleeding and patients undergoing chemotherapy;
(13) coagulation disorders selected from hypoprothrombinemia, haemophilia and other bleeding problems;
(14) kidney disease;
(15) thrombosis;
(16) occlusive vascular disease;
(17) presurgery; and
(18) anti-coagulation.

17. A method according to claim 16 wherein the prostaglandin mediated disease is selected from the group consisting of: pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, rheumatoid arthritis, degenerative joint diseases (osteoarthritis), gout and ankylosing spondylitis, bursitis, burns, radiation and corrosive chemical injuries, sunburns, pain following surgical and dental procedures as well as immune and autoimmune diseases.

18. A method according to claim 17 wherein the prostaglandin mediated disease is pain, fever or inflammation associated with dysmenorrhea.

19. A method according to claim 15, wherein the compound is co-administered with other agents or ingredients.

20. A method according to claim 19 wherein the compound is co-administered with another agent or ingredient selected from the group consisting of:
(1) an analgesic selected from acetaminophen, phenacetin, aspirin, a narcotic;
(2) a cyclooxygenase-2 selective nonsteroidal anti-inflammatory drug or a conventional nonsteroidal anti-inflammatory drug;
(3) caffeine;
(4) an $H_2$-antagonist;
(5) aluminum or magnesium hydroxide;
(6) simethicone;
(7) a decongestant selected from phenylephrine, phenylpropanolamine, pseudophedrine, oxymetazoline, ephinephrine, naphazoline, xylometazoline, propylhexedrine, or levo-desoxyephedrine;
(8) an antiitussive selected from codeine, hydrocodone, caramiphen, carbetapentane and dextramethorphan;
(9) another prostaglandin ligand selected from misoprostol, enprostil, rioprostil, ornoprostol and rosaprostol; a diuretic; and
(10) a sedating or non-sedating antihistamine.

21. A method according to claim 20 wherein the compound is co-administered with a cyclooxygenase-2 selective nonsteroidal anti-inflammatory drug or a conventional nonsteroidal anti-inflammatory drug.

22. A method according to claim 21 wherein the compound is co-administered with a conventional nonsteroidal anti-inflammatory drug selected from the group consisting of: aspirin, ibuprofen, naproxen, and ketoprofen.

23. A method according to claim 21 wherein the compound is co-administered with a cyclooxygenase-2 selective nonsteroidal anti-inflammatory drug selected from rofecoxib, MK-663, valdecoxib, parecoxib and celecoxib.

* * * * *